(12) United States Patent
Nguyen et al.

(10) Patent No.: US 11,181,660 B2
(45) Date of Patent: Nov. 23, 2021

(54) EVALUATING DRILL-IN FLUID PERFORMANCE IN A WELLBORE

(71) Applicant: Halliburton Energy Services, Inc., Houston, TX (US)

(72) Inventors: Philip D. Nguyen, Houston, TX (US); Weijun Guo, Houston, TX (US); Jay Paul Deville, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 64 days.

(21) Appl. No.: 16/742,024

(22) Filed: Jan. 14, 2020

(65) Prior Publication Data

US 2021/0215847 A1 Jul. 15, 2021

(51) Int. Cl.
| | |
|---|---|
| *G01V 5/10* | (2006.01) |
| *G01N 33/28* | (2006.01) |
| *G01N 23/22* | (2018.01) |
| *E21B 21/00* | (2006.01) |
| *E21B 47/11* | (2012.01) |

(52) U.S. Cl.
CPC ............ *G01V 5/101* (2013.01); *E21B 21/003* (2013.01); *E21B 47/11* (2020.05); *G01N 23/22* (2013.01); *G01N 33/2823* (2013.01); *G01N 2223/637* (2013.01)

(58) Field of Classification Search
CPC ....... E21B 21/003; E21B 47/11; G01N 23/22; G01N 33/2823; G01N 2223/637; G01V 5/101
See application file for complete search history.

(56) References Cited

U.S. PATENT DOCUMENTS

| | | | |
|---|---|---|---|
| 4,439,677 | A | 3/1984 | Martin |
| 4,691,772 | A | 9/1987 | Ebenhack et al. |
| 5,812,068 | A | 9/1998 | Wisler et al. |
| 5,909,774 | A | 6/1999 | Griffith et al. |
| 7,497,278 | B2 | 3/2009 | Schriener et al. |
| 7,678,742 | B2 | 3/2010 | Munoz et al. |

(Continued)

FOREIGN PATENT DOCUMENTS

WO 2015200401 12/2015

OTHER PUBLICATIONS

PCT Application No. PCT/US2020/013472, International Search Report and Written Opinion, dated Oct. 13, 2020, 13 pages.

*Primary Examiner* — Mark R Gaworecki
(74) *Attorney, Agent, or Firm* — Kilpatrick Townsend & Stockton LLP (57) ABSTRACT

A system includes a neutron source positionable within a wellbore to emit one or more neutrons toward a formation surrounding the wellbore. The system also includes a gamma ray detector positionable within the wellbore to detect gamma rays. Further, the system includes a gamma ray analyzer that can perform operations. The operations can include receiving data indicating detected gamma rays from the gamma ray detector. Additionally, the operations include determining, from the data indicating the detected gamma rays, an amount of activated tracer material present within the wellbore originating from non-radioactive tracer material of drill-in fluid. The operations also include determining, from the amount of activated tracer material, an amount of filtercake buildup in a wellbore, a depth of fluid-loss filtrate into the formation surrounding the wellbore, or a combination thereof.

20 Claims, 4 Drawing Sheets

(56) References Cited

U.S. PATENT DOCUMENTS

| | | |
|---|---|---|
| 8,881,808 B2 | 11/2014 | Dorffer et al. |
| 9,759,834 B2 | 9/2017 | Lee et al. |
| 9,864,092 B2 | 1/2018 | Torres-Verdin et al. |
| 10,042,082 B2 | 8/2018 | Luo et al. |
| 10,053,979 B2 | 8/2018 | Rasmus et al. |
| 10,061,054 B2 | 8/2018 | Jacobson et al. |
| 10,107,935 B2 | 10/2018 | Vasquez et al. |
| 2018/0011215 A1 | 1/2018 | Vasquez et al. |

EVALUATING DRILL-IN FLUID PERFORMANCE IN A WELLBORE

TECHNICAL FIELD

The present disclosure relates generally to techniques for evaluating drilling performance and, more particularly (although not necessarily exclusively), to evaluating performance of a drill-in fluid within a wellbore.

BACKGROUND

A well system (e.g., oil or gas) may include a wellbore drilled through a subterranean formation. The subterranean formation may include a reservoir permeated by oil or gas that is to be extracted using the well system. A drill-in operation may be performed when the wellbore reaches the reservoir within the formation. The drill-in operation may include a transition to using drill-in fluid during continued drilling in place of drilling fluid.

In an example, the drill-in fluid may be a fluid that minimizes damage to the reservoir and maximizes production in the zones exposed to the drill-in fluid. The drill-in fluid may be easily removable from the wellbore after completion of the drill-in operation. Monitoring removal of the drill-in fluid from the wellbore may provide a wellbore operator with information that is usable for enhancing production of hydrocarbons from the wellbore.

DETAILED DESCRIPTION

Certain aspects and examples of the present disclosure relate to determining an amount of filtercake or fluid-loss filtrate within a drill-in portion of a wellbore using gamma rays detected from activated tracer material within the filtercake or fluid-loss filtrate. In an example, the filtercake may be a buildup of drill-in fluid on a wellbore wall. The fluid-loss filtrate may be drill-in fluid that passes through the filtercake into a formation surrounding the wellbore. Further, the drill-in fluid may be a fluid used during a drilling operation through a hydrocarbon-bearing reservoir within the formation surrounding the wellbore. In an example, the drill-in fluid may be designed to minimize or reduce damage to the reservoir and maximize production of reservoir zones exposed to the drill-in fluid. The drill-in fluid may include a non-radioactive tracer material that is activated to emit gamma rays upon exposure to neutrons emitted from a neutron source.

Determining the amount of filtercake or fluid-loss filtrate at or within the drill-in portion of the wellbore can help quantify an impact of the drill-in fluid on well production performance. For example, such a determination may provide an operator of the wellbore with information about the removability of the drill-in fluid from the wellbore when preparing the wellbore for production. Further, the filtercake and fluid-loss filtrate may be measured immediately after drilling, after preparing the wellbore for production, upon completion of production, or any combination thereof. The techniques described herein may remove or otherwise limit uncertainties associated with presence of the filtercake and fluid-loss filtrate such that the wellbore operator is able to determine the impact of the drill-in fluid on the reservoir accurately.

Some aspects of the techniques may characterize and evaluate effectiveness of fluid-loss control of filtercake buildup generated by the drill-in fluid during a drilling operation within a reservoir portion of a wellbore. The techniques may also evaluate removal of the filtercake buildup before and during well production. Further, the techniques may evaluate a depth of fluid-loss filtrate invasion into the formation surrounding the wellbore during and after drill-in activity and the effects of the invasion on wellbore productivity.

The drill-in fluid compositions may include non-radioactive tracer materials. A neutron source may emit neutrons into a formation surrounding the wellbore, and the neutrons may activate the non-radioactive tracer materials present within filtercake on walls of the wellbore and within fluid-loss filtrate within the formation surrounding the wellbore. The gamma rays generated from the activated tracer materials may be measured by a gamma ray detector, and the measured gamma rays may be used to determine an impact of filtercake deposition, a degree of the removal of the filtercake deposition, and a depth of fluid-loss filtrate invasion in the formation. The resulting measurements may be used to determine the impact of the filtercake and the fluid-loss filtrate on the productivity of the wellbore.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

Figure 1:
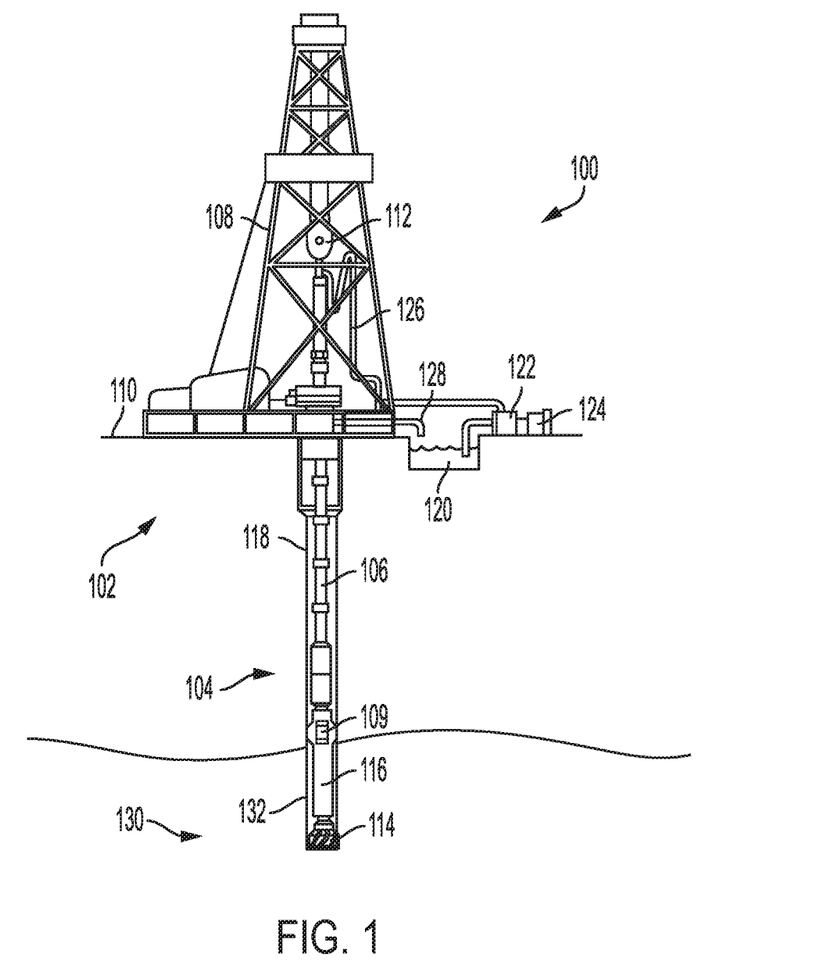
FIG. 1 is a cross-sectional view of a drilling system according to one example of the present disclosure.

FIG. 1 is a cross-sectional view of a drilling system 100 according to one example of the present disclosure. A wellbore may 118 be created by drilling into the formation 102 using the drilling system 100. The drilling system 100 may be operated to drive a bottom hole assembly (BHA) 104 positioned or otherwise arranged at a bottom of a drill string 106 extending into the formation 102 from a derrick 108 arranged at a surface 110. The derrick 108 includes a kelly 112 that can be used to lower and raise the drill string 106. The BHA 104 may include a drill bit 114 operatively coupled to a drilling tool 116, which can be moved axially within the wellbore 118 as attached to or part of the drill string 106. The drill string may include one or more sensors 109 to obtain measurements associated with conditions of the drill bit and wellbore. The measurements may be returned to the surface through cabling (not shown) or by one or more wireless transceivers (not shown). Sensors 109 can include, by example only, any sensor that produces a signal of characteristic associated with the drilling tool 116, the wellbore 118, or subterranean environment.

During drilling operations, the drill bit 114 penetrates the formation 102 and thereby creates the wellbore 118. The BHA 104 provides control of the drill bit 114 as it advances into the formation 102. Drilling fluid or "mud" from mud tank 120 may be pumped downhole using a mud pump 122 powered by an adjacent power source, such as a prime mover or motor 124. The drilling fluid may be pumped from the mud tank 120, through a stand pipe 126, which feeds the mud into drill string 106 and conveys the drill fluid to the drill bit 114. The mud exits one or more nozzles (not shown) arranged in the drill bit 114. After exiting the drill bit 114, the mud circulates back to the surface 110 via an annulus defined between the wellbore 118 and the drill string 106, and in the process returns drill cuttings and debris to the surface 110. The cuttings and mud mixture are passed through a flow line 128 and are processed such that a cleaned mud is returned down hole through the stand pipe 126.

Drilling fluids may perform a number of functions within the wellbore in addition to removing cuttings from the wellbore. For instance, a drilling fluid composition may be designed to cool the drill bit, lubricate the drill bit and wellbore, minimize formation damage, remove cuttings, suspend cuttings within the drilling fluid when drilling operations are halted, control corrosion, control formation pressures, seal permeable formations, maintain wellbore stability, minimize environment contamination, combinations thereof, and the like. In some instances, the particular composition of the drilling fluid may be based on characteristics of the subterranean environment and the drill bit. For instance, the drilling fluid composition may be selected to ensure it is thixotropic such that a halt in operations does not allow the cuttings to sink to the bottom of the wellbore. If the cuttings are allowed to sink, unintended bridging can occur, which may cause wellbore cleaning problems and stuck pipe.

When the drill bit 114 reaches a reservoir 130 within the formation 102, the drilling operation may replace the drilling fluid with a drill-in fluid. The drill-in fluid may be a type of drilling mud that is designed for drilling through the reservoir 130 containing hydrocarbons. In an example, the drill-in fluid may minimize damage to the reservoir 130 and maximize hydrocarbon production in zones exposed to the drill-in fluid as compared with other portions of the wellbore 118 that are drilled using drilling fluid. The drill-in fluid may include a base fluid, a viscosifier, a relative permeability modifier fluid loss control additive, and a degradable bridging agent including a degradable material capable of undergoing an irreversible degradation downhole.

During the drilling operation through the reservoir 130, the drill-in fluid may form a filtercake on a wall of the wellbore 118 that includes an acid-soluble portion (e.g., the degradable bridging agent such as calcium carbonate bridging solids) and a polymeric portion (e.g., the viscosifier and the relative permeability modifier fluid loss control additive). Further, to detect the presence of the filtercake 132 on the wall of the wellbore a non-radioactive tracer material may also be present in the drill-in fluid and the resulting filtercake 132.

In an example, the sensor 109 may include a neutron source (not shown) and a gamma ray detector (not shown). The neutron source may emit neutrons toward the formation 102, and the neutrons may temporarily activate the non-radioactive tracer material in the filtercake 132. The activated tracer material of the filtercake 132 may emit gamma rays in response to the activation, and the gamma ray detector of the sensor 109 may detect the gamma rays emitted by the activated tracer material of the filtercake 132. Based on the detected gamma rays emitted by the activated tracer material of the filtercake 132, a wellbore operator may determine a thickness of the filtercake 132 or a degree of buildup of the filtercake 132 within the wellbore 118 upon completion of the drill-in process. For example, an expected gamma ray count associated with varying thicknesses of the filtercake 132 may be known, and the detected count of gamma rays by the sensor 109 may be compared to the expected gamma ray counts associated with the varying thicknesses of the filtercake 132 to estimate the thickness of the filtercake 132 within the wellbore 118.

The drill-in fluid may also generate a fluid-loss filtrate, as depicted below in FIG. 3. The fluid-loss filtrate may be a leakage of solid particles of the drill-in fluid into the reservoir 130 during the drill-in process. The extent of the fluid-loss filtrate (e.g., a depth of invasion or penetration) may be determined using the neutron source and the gamma ray detector of the sensor 109 in a manner similar to determining the thickness or degree of buildup of the filtercake 132. That is, the non-radioactive tracer material of the drill-in fluid may invade the reservoir 130 during leakage of the drill-in fluid into the reservoir 130, and neutrons emitted from the neutron source may temporarily activate the non-radioactive tracer material. The activated tracer material of the fluid-loss filtrate may emit gamma rays in response to being activated, and the gamma ray detector of the sensor 109 may detect the gamma rays emitted by the activated tracer material of the fluid-loss filtrate.

Based on the detected gamma rays emitted by the activated tracer material of the fluid-loss filtrate, a wellbore operator may determine the depth of invasion of the fluid-loss filtrate within the reservoir 130 upon completion of the drill-in process. For example, various calculations to determine the depth of invasion of the fluid-loss filtrate within the reservoir 130 may be based on fluid leakoff volume, formation permeability, and differential pressure. An inversion of a sensitivity of gamma detection of the filtrate in the formation 102 may provide a mechanism for determining the depth of invasion of the fluid-loss filtrate within the reservoir 130.

In an example, the non-radioactive tracer material of the drill-in fluid may be an element from Groups I to VIII of the Periodic Table of Elements, an element from the lanthanide series, any derivative thereof, and any combination thereof. In another example, the non-radioactive tracer material may be aluminum, barium, beryllium, cadmium, cerium, chromium, cobalt, copper, dysprosium, erbium, europium, gadolinium, gold, holmium, iodine, iridium, lanthanum, lead, lutetium, magnesium, manganese, molybdenum, neodymium, nickel, phosphorous, praseodymium, promethium, rhenium, samarium, silver, technetium, terbium, thulium, titanium, tungsten, vanadium, ytterbium, zinc, any derivative thereof, and any combination thereof. Further, the non-radioactive tracer material is present in an amount from 0.01% to 1% weight by volume of the drill-in fluid.

The base fluid of the drill-in fluid may be aqueous, such as an aqueous fluid. In an example, the base fluid may include fresh water, saltwater, bring (e.g., saturated saltwater), or seawater. Additionally, the base fluid may include a high density brine made from sodium chloride, sodium bromide, zinc bromide, or formats (e.g., sodium, potassium, or cesium) to minimize reliance on solid weighting agents. Generally, the water may be from any source provided that it does not contain components that may adversely affect other components of the drill-in fluid. In an example, the base fluid of the drill-in fluid may also be non-aqueous such as an oil-base fluid.

The viscosifier of the drill-in fluid may be included in the drill-in fluid to increase a viscosity of the drill-in fluid. Examples of the viscosifier may include: biopolymers such as xanthan, scleroglucan, and succinoglycan; cellulose derivatives such as hydroxyethylcellulose and nanocellulose; and guar and its derivatives such as hydroxypropyl guar. Combinations and derivatives of these are suitable as well. The viscosifier is present in the drill-in fluids of the present invention in an amount that is sufficient to suspend the bridging agent and drill cuttings in the drill-in fluid. More particularly, the viscosifier may be present in the drill-in fluids of the present invention in an amount in the range of from about 0.01% to about 1% by weight.

A relative permeability modifier fluid loss control additive, also referred to as a relative permeability modifier, may be included in the drill-in fluid and attach to surfaces within a porosity of the reservoir 130 to reduce the permeability of the portion of the reservoir 130 to aqueous fluids without substantially changing the permeability of the reservoir 130 to hydrocarbons. Examples of relative permeability modifiers include at least one relative permeability modifier selected from the group consisting of: a water-soluble, hydrophobically modified polymer; a water-soluble, hydrophilically modified polymer; a water-soluble polymer without hydrophobic or hydrophilic modification; and any combination thereof. The hydrophobically modified polymer may include an amino methacrylate/alkyl amino methacrylate copolymer. In another example, a relative permeability modifier includes a reaction product of 1) an acrylamide polymer, any copolymer thereof, any derivative thereof, any salt thereof, or any combination thereof, and 2) a plurality of amine-containing compounds or any salt thereof, each amine-containing compound containing a primary amine, a secondary amine, or any combination thereof, and the amine-containing compounds being randomly reacted through transamidation with at least a portion of the amide groups of the acrylamide polymer.

A degradable bridging agent of the drill-in fluid may include degradable material capable of undergoing an irreversible degradation downhole. The bridging agent may be suspended in the drill-in fluid, and, as the drill-in fluid begins to form a filter cake within the subterranean formation, the bridging agent may be distributed in the resulting filtercake 132. In some examples, the filtercake 132 forms on the wall of the wellbore 118. After a requisite time period dictated by the characteristics of the particular degradable bridging agent, the degradable bridging agent degrades. This degradation, in effect, causes the degradable bridging agent to be removed from the filter cake. As a result, voids are created in the filtercake 132 to enable produced fluids from the reservoir 130 to flow more freely.

The degradable bridging agents may include a degradable material. Non-limiting examples of suitable degradable materials include, but are not limited to, degradable polymers, dehydrated compounds, or mixtures of the two. Combinations and derivatives of these may be suitable for use as the degradable bridging agents as well.

Figure 2:
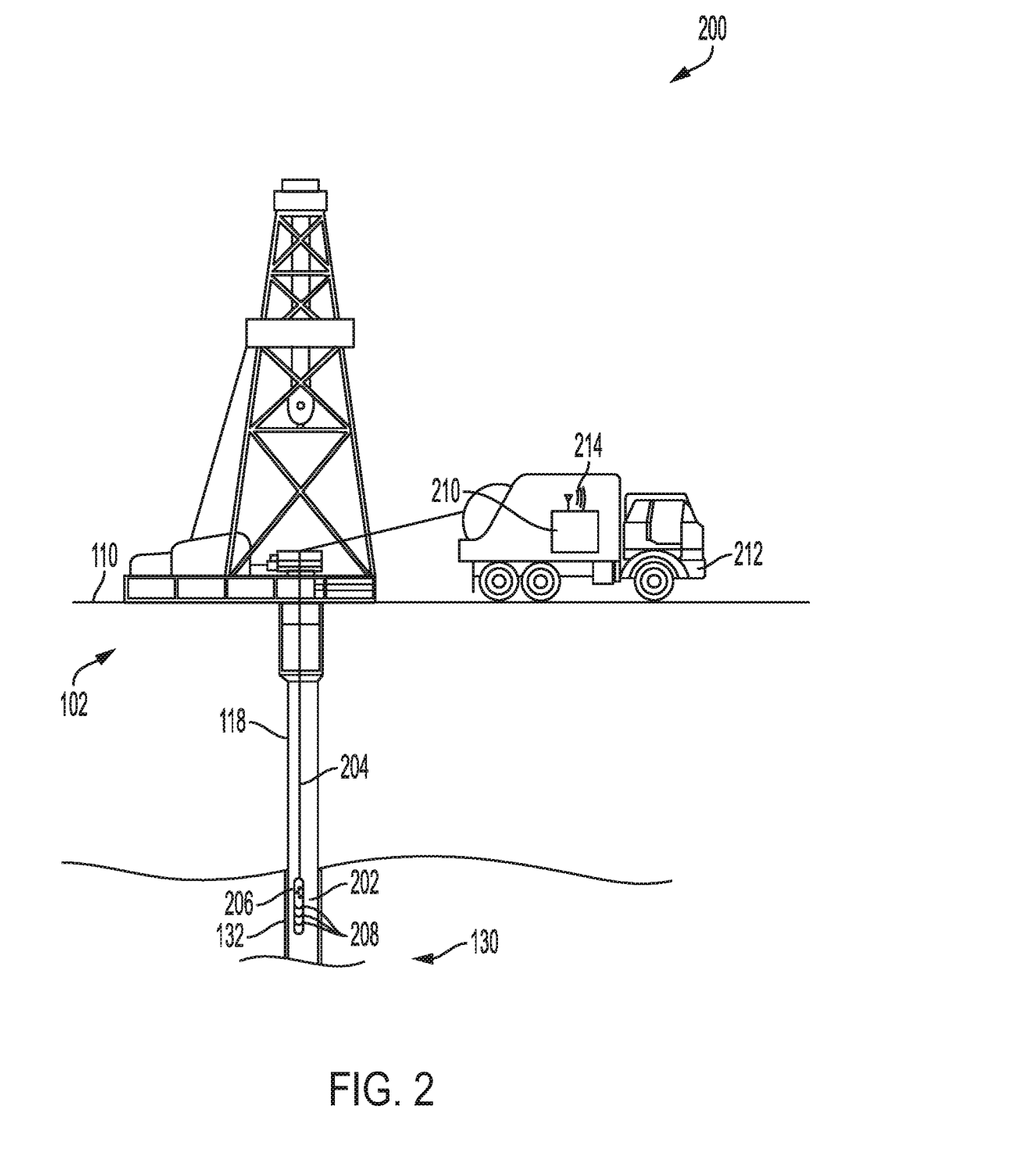
FIG. 2 is a cross-sectional view of a wellbore system including a wireline logging operation according to one example of the present disclosure.

FIG. 2 is a cross-sectional view of a wellbore system 200 including a wireline logging operation according to one example of the present disclosure. Upon completing the drill-in operation of the wellbore 118, the well system 200 may deploy a gamma ray detection system 202 within the wellbore 118. The gamma ray detection system 202 may be deployed using a wireline 204, as illustrated, or the gamma ray detection system 202 may be deployed using a slickline, coiled tubing, a downhole tractor, or drill pipe. The gamma ray detection system 202 may operate in a similar manner to the sensor 109, as described above with respect to FIG. 1, to detect a depth of buildup of the filtercake 132 or an invasion depth of a fluid-loss filtrate into the reservoir 130.

In an example, the gamma ray detection system 202 may include a neutron source 206 and one or more gamma ray detectors 208. The neutron source 206 emits neutrons into an area surrounding the gamma ray detection system 202. The emitted neutrons may interact with the non-radioactive tracer material of the filtercake 132 or the fluid-loss filtrate to activate the non-radioactive tracer material. Upon activation, the activated tracer material temporarily emits gamma rays, which can be detected by the gamma ray detectors 208. Using three gamma ray detectors 208 in a linear arrangement, as illustrated in FIG. 2, the gamma-rays may be detected. For example, tracer gamma-ray counts may be acquired through a spectroscopy processing algorithm, and the counts may be proportional to an amount of the non-radioactive tracer material in the wellbore.

The gamma ray detection system 202 may be in communication with a computing device 210 (e.g., a gamma ray analyzer), which is illustrated by way of example at the surface 110 in FIG. 2. In an additional embodiment, the computing device 210 may be located elsewhere, such as downhole, or the computing device may be a distributed computing system including multiple, spatially separated computing components. Other equipment of the well system 200 described herein may also be in communication with the computing device 210. In some embodiments, one or more processors used to control a production or injection operation of the well system 200 may be in communication with or otherwise controlled by the computing device 210.

In FIG. 2, the computing device 210 is illustrated as being deployed in a work vehicle 212. However, the computing device 210 that receives data from the gamma ray detection system 202 may be permanently installed surface equipment of the well system 200. In other embodiments, the computing device 210 may be hand-held or remotely located from the well system 200. In some examples, the computing device 210 may process at least a portion of the data received and transmit the processed or unprocessed data to an additional computing device via a wired or wireless network. The additional computing device may be offsite, such as at a data-processing center. The additional computing device may receive the data, process the data, execute computer program instructions to issue commands to control the operation of the well system 200, and communicate those commands to computing device 210.

The computing device 210 may be positioned belowground, aboveground, onsite, in a vehicle, offsite, etc. The computing device 210 may include a processor interfaced with other hardware via a bus. A memory, which may include any suitable tangible (and non-transitory) computer-readable medium, such as RAM, ROM, EEPROM, or the like, can embody program components that configure operation of the computing device 210. In some aspects, the computing device 210 may include input/output interface components (e.g., a display, printer, keyboard, touch-sensitive surface, and mouse) and additional storage.

The computing device 210 may include a surface communication device 214. The surface communication device 214 may represent one or more of any components that facilitate a network connection. In the example shown in FIG. 2, the surface communication device 214 is wireless and may include wireless interfaces such as IEEE 802.11, Bluetooth, or radio interfaces for accessing cellular telephone networks (e.g., RF stage/antenna for accessing a CDMA, GSM, UMTS, or other mobile communications network). In some examples, the surface communication device 214 may use acoustic waves, surface waves, vibrations, optical waves, or induction (e.g., magnetic induction)

for engaging in wireless communications. In other examples, the surface communication device 214 may be wired and can include interfaces such as Ethernet, USB, IEEE 1394, or a fiber optic interface. The computing device 210 can receive wired or wireless communications from other computing devices and perform one or more tasks based on the communications.

While FIG. 2 depicts the well system 200 where the computing device 210 receives data from the gamma ray detection system 202 for use in determining the presence of the filtercake 132 or the fluid-loss filtrate in the reservoir 130, other systems may be controlled using the computing device 210. For example, the computing device 210 may receive performance data related to hydrocarbon production systems, wellbore casing and cementing systems, wellbore fracturing systems, wellbore maintenance programs, drilling systems, or any other wellbore technologies. The computing device 210 may receive the performance data, execute computer program instructions to issue commands to control the operation of the wellbore technology, and apply those commands to equipment of the wellbore technology. In some aspects, the performance data may be considered "real-time" data as the performance data is collected and transmitted to the computing device 210 as the wellbore equipment is operated. In some instances, the presence and magnitude of the filtercake 132 or the fluid-loss filtrate in the reservoir 130 may be used as at least a portion of the performance data used to control the hydrocarbon production systems, wellbore casing and cementing systems, wellbore fracturing systems, wellbore maintenance programs, drilling systems, or any other wellbore technologies.

Further, while FIGS. 1 and 2 depict the wellbore 118 in a vertical orientation, the techniques described herein may also be used in horizontal wellbore systems. As used herein, the horizontal wellbore system may be a wellbore with a trajectory other than vertical (e.g., horizontal, inclined, etc.).

Figure 3:
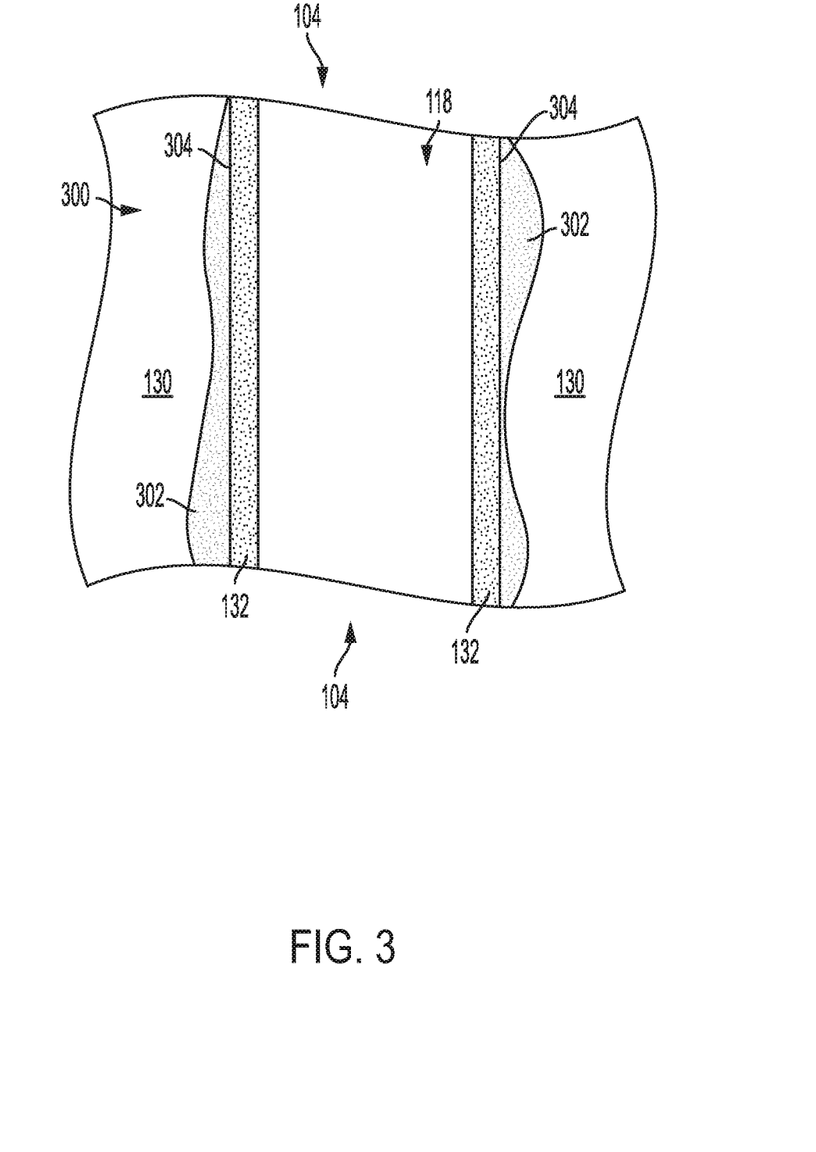
FIG. 3 is a cross-sectional view of a drill-in portion of a formation surrounding a wellbore including a filtercake and fluid-loss filtrate according to one example of the present disclosure.

FIG. 3 is a cross-sectional view of a drill-in portion 300 of the formation 102 surrounding the wellbore 118 including the filtercake 132 and fluid-loss filtrate 302 according to one example of the present disclosure. During the drill-in operation within the drill-in portion 300 of the formation 102 (e.g., at the reservoir 130), the drill-in fluid may be pressed against a wall 304 of the wellbore 118. The pressure on the drill-in fluid against the wall 304 can result in a buildup of the filtercake 132. Additionally, particulate material from the drill-in fluid may invade or penetrate the reservoir 130 during the drill-in operation, which may result in formation of the fluid-loss filtrate 302.

Presence of either or both of the filtercake 132 and the fluid-loss filtrate 302 may impact efficiency of hydrocarbon production from the reservoir 130. Accordingly, monitoring the thickness of the filtercake 132 and a depth of invasion of the fluid-loss filtrate 302 using the techniques described herein may provide a wellbore operator with information usable to improve the production efficiency of the well system 200. For example, if the wellbore operator detects the presence of a thick filtercake 132 prior to beginning hydrocarbon production, the wellbore operator may take additional action to remove the filtercake 132 from the wellbore 118. Additionally, if the wellbore operator detects that the fluid-loss filtrate 302 has a significant invasion depth within the reservoir 130, the wellbore operator can implement remedial measures to improve hydrocarbon production efficiency. For example, a higher concentration of fluid loss control additive may be applied to the drill-in fluid to address invasion of the fluid-loss filtrate 302 into the reservoir 130. The fluid loss control additive may be degradable to ensure that no permanent damage results from further fluid-loss control and flow paths for hydrocarbon production are maintained. In another example, surfactants may be added to the drill-in fluid to reduce surface tension of the drill-in fluid. This reduced surface tension of the drill-in fluid may be implemented to overcome waterblocks or emulsions in the formation resulting from invasion of the fluid-loss filtrate 302 into the reservoir 130.

Figure 4:
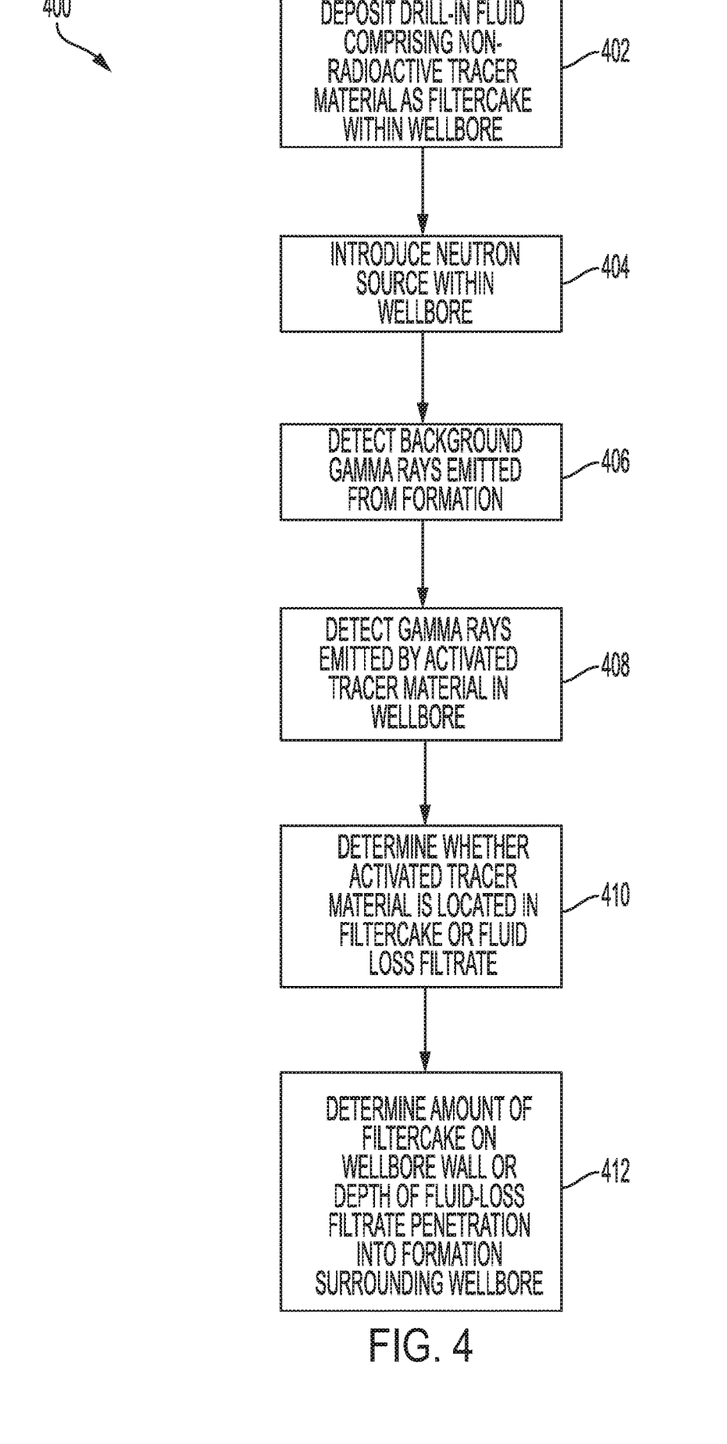
FIG. 4 is a flowchart of a process for determining an amount of filtercake or fluid-loss filtrate within the wellbore according to one example of the present disclosure.

FIG. 4 is a flowchart of a process 400 for determining an amount of the filtercake 132 or the fluid-loss filtrate 302 within or surrounding the wellbore 118 according to one example of the present disclosure. In an example, the process 400 may occur after the drill-in operation is completed, during production, or after production is completed. For illustrative purposes, the process 400 is described with reference to certain examples depicted in the figures. Other implementations, however, are possible.

At block 402, the process 400 involves depositing the drill-in fluid within the wellbore 118. As discussed above, the drill-in fluid may include a non-radioactive tracer material. Further, during a drill-in operation of the wellbore 118 within the reservoir 130, the drill-in fluid may build up on the wall 304 of the wellbore 118 as the filtercake 132. Particulate material of the drill-in fluid may also penetrate the wall 304 of the wellbore 118 and invade the reservoir 130 resulting in the fluid-loss filtrate 302.

At block 404, the process 400 involves introducing the neutron source 206 within the wellbore 118. The neutron source 206 may emit neutrons into an area surrounding the neutron source 206. In an example, the emitted neutrons are used to activate the non-radioactive tracer material of the drill-in fluid such that an amount of the filtercake 132 and a magnitude of the fluid-loss filtrate 302 can be detected.

At block 406, the process 400 involves detecting background gamma rays emitted from the formation 102. The background gamma rays may be detected using one or more of the gamma ray detectors 208, and the background gamma rays may be detected from a portion of the formation 102 that is not part of the drill-in portion 300 of the formation 102. In an example, the detected background gamma rays may enable establishment of a background energy spectrum of the formation 102 (e.g., at an area where the non-radioactive tracer material is not present within the wellbore 118).

At block 408, the process 400 involves detecting gamma rays emitted by activated tracer material in the wellbore 118. The activated tracer material may be generated when the emitted neutrons from the neutron source 206 interact with the non-radioactive tracer material of the filtercake 132 or the fluid-loss filtrate 302. Upon activation, the activated tracer material emits gamma rays, which are detectable by the gamma ray detectors 208.

At block 418, the process 400 involves determining whether the activated tracer material generating the detected gamma rays is located in the filtercake 132, in the fluid-loss filtrate 302, or a combination of the two. The location of the gamma rays may be determined based on depth or shallowness of the gamma ray detection. For example, shallow gamma rays may be emitted from the filtercake, while deeper gamma rays may be emitted from the fluid-loss filtrate. In some examples, the material producing the gamma rays may be different. For example, the drill-in fluid may include both insoluble tracer materials and soluble tracer materials, where the insoluble and soluble tracer materials are measured differently. The insoluble tracer materials may remain in the filtercake 132, and measurements of gamma rays originating from the insoluble materials may provide information about the filtercake 132. The soluble tracer materials (or very small insoluble tracer materials) may extend into the fluid-loss filtrate 302. Accordingly, measurements of gamma rays originating from the soluble tracer materials may provide information about the fluid-loss filtrate 302.

At block 412, the process 400 involves determining an amount of the filtercake 132 on the wall 304 of the wellbore 118, a depth of the fluid-loss filtrate 302 within the reservoir 130 of the formation 102 surrounding the wellbore 118, or both. The amount of the filtercake 132 may be a measurement of a thickness of the filtercake 132 on the wall 304 of the wellbore 118. Further, the depth of the fluid-loss filtrate 302 within the reservoir 130 may provide an indication of how deep into the reservoir 130 the particulate matter of the drill-in fluid penetrated.

Because the background energy spectrum for the formation is determined at block 406 based on the background gamma rays of the formation 102, the background energy spectrum may be corrected for when the gamma ray detectors 208 detect the gamma rays from the active tracer material. Accordingly, the background gamma rays of the formation 102 are not included when determining the thickness of the filtercake 132 or the depth of the fluid-loss filtrate 302 into the reservoir 130.

In some aspects, a system and method for measuring filtercake and fluid-loss filtrate within a wellbore are provided according to one or more of the following examples:

As used below, any reference to a series of examples is to be understood as a reference to each of those examples disjunctively (e.g., "Examples 1-4" is to be understood as "Examples 1, 2, 3, or 4").

Example 1 is a system comprising: a neutron source positionable within a wellbore to emit one or more neutrons toward a formation surrounding the wellbore; a gamma ray detector positionable within the wellbore to detect gamma rays; a gamma ray analyzer comprising one or more processors and a non-transitory computer-readable medium storing instructions that are executable by the one or more processors to cause the gamma ray analyzer to perform operations including: receiving data indicating detected gamma rays from the gamma ray detector; determining, from the data indicating the detected gamma rays, an amount of activated tracer material present within the wellbore that originates from non-radioactive tracer material of drill-in fluid; and determining, from the amount of activated tracer material, an amount of filtercake buildup on a wellbore wall, a depth of fluid-loss filtrate into the formation surrounding the wellbore, or a combination thereof.

Example 2 is the system of example 1, wherein the gamma ray analyzer is positionable at a surface of the wellbore.

Example 3 is the system of examples 1-2, wherein the neutron source and the gamma ray detector are coupleable to a wireline, a slickline, coiled tubing, a downhole tractor, or drill pipe.

Example 4 is the system of examples 1-3, wherein the neutron source is positionable within the wellbore to activate the non-radioactive tracer material of the filtercake or the fluid-loss filtrate to generate the activated tracer material that emits the gamma rays detected by the gamma ray detector.

Example 5 is the system of examples 1-4, wherein the non-radioactive tracer material comprises an element selected from the group consisting of: an element from Groups I to VIII, an element from the lanthanide series, any derivative thereof, and any combination thereof.

Example 6 is the system of examples 1-5, wherein the drill-in fluid comprises an aqueous base fluid and the non-radioactive tracer material.

Example 7 is the system of examples 1-6, wherein the non-radioactive tracer material is present in an amount from 0.01% to 1% weight by volume of the drill-in fluid.

Example 8 is the system of examples 1-7, wherein the gamma ray detector comprises a set of three gamma ray detectors in a linear arrangement.

Example 9 is a method, comprising: depositing a drill-in fluid comprising a non-radioactive tracer material into a wellbore within a drill-in portion of a formation during a drill-in operation; emitting, by a neutron source, neutrons into a drill-in portion of the formation surrounding the wellbore to generate activated tracer material from the non-radioactive tracer material; receiving, at a gamma ray detector, gamma rays from the activated tracer material; determining whether the gamma rays originate from the activated tracer material located within a filtercake, from the activated tracer material located within a fluid-loss filtrate, or both; and determining, using data associated with the gamma rays, an amount of filtercake buildup of the filtercake on a wellbore wall, a depth of the fluid-loss filtrate into the formation surrounding the wellbore, or a combination thereof.

Example 10 is the method of example 9, wherein the drill-in portion of the formation comprises a reservoir containing hydrocarbons.

Example 11 is the method of examples 9-10, further comprising: emitting, by the neutron source, neutrons into the a second portion of the formation different from the drill-in portion of the formation; receiving, at the gamma ray detector, background gamma rays from the formation; establishing, using data associated with the background gamma rays, a background energy spectrum of the formation; and determining, using the data associated with the gamma rays and the background energy spectrum, the amount of filtercake buildup, the depth of the fluid-loss filtrate, or the combination thereof.

Example 12 is the method of examples 9-11, wherein the drill-in fluid further comprises an aqueous base fluid, a viscosifier, a relative permeability modifier fluid loss control additive, and a degradable bridging agent comprising a degradable material capable of undergoing an irreversible degradation downhole.

Example 13 is the method of examples 9-12, wherein the non-radioactive tracer material comprises an element selected from the group consisting of: aluminum, barium, beryllium, cadmium, cerium, chromium, cobalt, copper, dysprosium, erbium, europium, gadolinium, gold, holmium, iodine, iridium, lanthanum, lead, lutetium, magnesium, manganese, molybdenum, neodymium, nickel, phosphorous, praseodymium, promethium, rhenium, samarium, silver, technetium, terbium, thulium, titanium, tungsten, vanadium, ytterbium, zinc, any derivative thereof, and any combination thereof.

Example 14 is the method of examples 9-13, wherein the non-radioactive tracer material comprises an element selected from the group consisting of: an element from Groups I to VIII, an element from the lanthanide series, any derivative thereof, and any combination thereof.

Example 15 is the method of examples 9-14, further comprising: conveying the neutron source and the gamma ray detector downhole within the wellbore using a wireline, a slickline, coiled tubing, a downhole tractor, or drill pipe.

Example 16 is a drill-in fluid, comprising: a base fluid; a viscosifier; a relative permeability modifier fluid loss control additive, a degradable bridging agent comprising a degradable material capable of undergoing an irreversible degradation downhole, or both; and a non-radioactive tracer material capable of being activated by exposure to neutrons to generate an activated tracer material that emits gamma rays that are detectable by a gamma ray detector within a wellbore.

Example 17 is the drill-in fluid of example 16, wherein the non-radioactive tracer material comprises an element selected from the group consisting of: an element from Groups I to VIII, an element from the lanthanide series, any derivative thereof, and any combination thereof.

Example 18 is the drill-in fluid of examples 16-17, wherein the non-radioactive tracer material comprises an element selected from the group consisting of: aluminum, barium, beryllium, cadmium, cerium, chromium, cobalt, copper, dysprosium, erbium, europium, gadolinium, gold, holmium, iodine, iridium, lanthanum, lead, lutetium, magnesium, manganese, molybdenum, neodymium, nickel, phosphorous, praseodymium, promethium, rhenium, samarium, silver, technetium, terbium, thulium, titanium, tungsten, vanadium, ytterbium, zinc, any derivative thereof, and any combination thereof.

Example 19 is the drill-in fluid of examples 16-18, wherein the non-radioactive tracer material is present in an amount from 0.01% to 1% weight by volume of the drill-in fluid.

Example 20 is the drill-in fluid of examples 16-19, wherein the gamma rays that are detectable by the gamma ray detector are capable of being analyzed to determine filtercake buildup on a wellbore wall of the wellbore, a depth of fluid-loss filtrate into a formation surrounding the wellbore, or a combination thereof.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system comprising:
   a neutron source positionable within a wellbore to emit one or more neutrons toward a formation surrounding the wellbore;
   a gamma ray detector positionable within the wellbore to detect gamma rays;
   a gamma ray analyzer comprising one or more processors and a non-transitory computer-readable medium storing instructions that are executable by the one or more processors to cause the gamma ray analyzer to perform operations including:
      receiving data indicating detected gamma rays from the gamma ray detector;
      determining, from the data indicating the detected gamma rays, an amount of activated tracer material present within the wellbore that originates from non-radioactive tracer material of drill-in fluid; and
      determining, from the amount of activated tracer material, an amount of filtercake buildup on a wellbore wall, a depth of fluid-loss filtrate into the formation surrounding the wellbore, or a combination thereof.

2. The system of claim 1, wherein the gamma ray analyzer is positionable at a surface of the wellbore.

3. The system of claim 1, wherein the neutron source and the gamma ray detector are coupleable to a wireline, a slickline, coiled tubing, a downhole tractor, or drill pipe.

4. The system of claim 1, wherein the neutron source is positionable within the wellbore to activate the non-radioactive tracer material of the filtercake or the fluid-loss filtrate to generate the activated tracer material that emits the gamma rays detected by the gamma ray detector.

5. The system of claim 1, wherein the non-radioactive tracer material comprises an element from the lanthanide series.

6. The system of claim 1, wherein the drill-in fluid comprises an aqueous base fluid and the non-radioactive tracer material.

7. The system of claim 1, wherein the non-radioactive tracer material is present in an amount from 0.01% to 1% weight by volume of the drill-in fluid.

8. The system of claim 1, wherein the gamma ray detector comprises a set of three gamma ray detectors in a linear arrangement.

9. A method, comprising:
   depositing a drill-in fluid comprising a non-radioactive tracer material into a wellbore within a drill-in portion of a formation during a drill-in operation;
   emitting, by a neutron source, neutrons into a drill-in portion of the formation surrounding the wellbore to generate activated tracer material from the non-radioactive tracer material;
   receiving, at a gamma ray detector, gamma rays from the activated tracer material;
   determining whether the gamma rays originate from the activated tracer material located within a filtercake, from the activated tracer material located within a fluid-loss filtrate, or both; and
   determining, using data associated with the gamma rays, an amount of filtercake buildup of the filtercake on a wellbore wall, a depth of the fluid-loss filtrate into the formation surrounding the wellbore, or a combination thereof.

10. The method of claim 9, wherein the drill-in portion of the formation comprises a reservoir containing hydrocarbons.

11. The method of claim 9, further comprising:
   emitting, by the neutron source, neutrons into a second portion of the formation different from the drill-in portion of the formation;
   receiving, at the gamma ray detector, background gamma rays from the formation;
   establishing, using data associated with the background gamma rays, a background energy spectrum of the formation; and
   determining, using the data associated with the gamma rays and the background energy spectrum, the amount of filtercake buildup, the depth of the fluid-loss filtrate, or the combination thereof.

12. The method of claim 9, wherein the drill-in fluid further comprises an aqueous base fluid, a viscosifier, a relative permeability modifier fluid loss control additive, and a degradable bridging agent comprising a degradable material capable of undergoing an irreversible degradation downhole.

13. The method of claim 9, wherein the non-radioactive tracer material comprises an element selected from the group consisting of:
   aluminum, barium, beryllium, cadmium, cerium, chromium, cobalt, copper, dysprosium, erbium, europium, gadolinium, gold, holmium, iodine, iridium, lanthanum, lead, lutetium, magnesium, manganese, molybdenum, neodymium, nickel, phosphorous, praseodymium, promethium, rhenium, samarium, silver, technetium, terbium, thulium, titanium, tungsten, vanadium, ytterbium, zinc, any derivative thereof, and any combination thereof.

14. The method of claim 9, wherein the non-radioactive tracer material comprises an element from the lanthanide series.

15. The method of claim 9, further comprising:
conveying the neutron source and the gamma ray detector downhole within the wellbore using a wireline, a slickline, coiled tubing, a downhole tractor, or drill pipe.

16. The method of claim 9, wherein the non-radioactive tracer material comprises an element from the lanthanide series.

17. A drill-in fluid, comprising:
a base fluid;
a viscosifier;
a relative permeability modifier fluid loss control additive, a degradable bridging agent comprising a degradable material capable of undergoing an irreversible degradation downhole, or both; and
a non-radioactive tracer material capable of being activated by exposure to neutrons to generate an activated tracer material that emits gamma rays that are detectable by a gamma ray detector within a wellbore;
wherein the gamma rays that are detectable by the gamma ray detector are capable of being analyzed to determine filtercake buildup on a wellbore wall of the wellbore, a depth of fluid-loss filtrate into a formation surrounding the wellbore, or a combination thereof.

18. The drill-in fluid of claim 17, wherein the non-radioactive tracer material comprises an element from the lanthanide series.

19. The drill-in fluid of claim 17, wherein the non-radioactive tracer material comprises an element selected from the group consisting of:
aluminum, barium, beryllium, cadmium, cerium, chromium, cobalt, copper, dysprosium, erbium, europium, gadolinium, gold, holmium, iodine, iridium, lanthanum, lead, lutetium, magnesium, manganese, molybdenum, neodymium, nickel, phosphorous, praseodymium, promethium, rhenium, samarium, silver, technetium, terbium, thulium, titanium, tungsten, vanadium, ytterbium, zinc, any derivative thereof, and any combination thereof.

20. The drill-in fluid of claim 17, wherein the non-radioactive tracer material is present in an amount from 0.01% to 1% weight by volume of the drill-in fluid.

* * * * *